(12) United States Patent
Geissler et al.

(10) Patent No.: US 9,387,020 B2
(45) Date of Patent: Jul. 12, 2016

(54) BONE PLATE SYSTEM FOR REPAIR OF PROXIMAL HUMERAL FRACTURE

(75) Inventors: William B. Geissler, Brandon, MS (US); Linda C. Cooper, Austin, TX (US)

(73) Assignee: Ascension Orthopedics, Inc., Austin, TX (US)

( * ) Notice: Subject to any disclaimer, the term of this patent is extended or adjusted under 35 U.S.C. 154(b) by 674 days.

(21) Appl. No.: 13/346,006

(22) Filed: Jan. 9, 2012

(65) Prior Publication Data

US 2012/0179208 A1    Jul. 12, 2012

Related U.S. Application Data

(60) Provisional application No. 61/431,258, filed on Jan. 10, 2011.

(51) Int. Cl.
*A61B 17/80* (2006.01)
*A61B 17/86* (2006.01)

(52) U.S. Cl.
CPC ......... *A61B 17/8042* (2013.01); *A61B 17/8061* (2013.01); *A61B 17/8625* (2013.01)

(58) Field of Classification Search
CPC ............. A61B 17/746; A61B 17/8014; A61B 17/8042; A61B 17/8061; A61B 17/7058; A61B 17/7059; A61B 17/80; A61B 17/8004; A61B 17/8033; A61B 17/74; A61B 17/742
USPC ............... 606/65, 66, 280, 71, 282, 286, 289, 606/295, 296
See application file for complete search history.

(56) References Cited

U.S. PATENT DOCUMENTS

| | | | |
|---|---|---|---|
| 3,842,825 A * | 10/1974 | Wagner | 606/66 |
| 4,493,317 A | 1/1985 | Klaue | |
| 4,565,193 A * | 1/1986 | Streli | 606/297 |
| 4,794,918 A | 1/1989 | Wolter | |
| 4,867,144 A | 9/1989 | Karas et al. | |
| 4,973,332 A | 11/1990 | Kummer | |
| 5,021,056 A | 6/1991 | Hofmann et al. | |

(Continued)

FOREIGN PATENT DOCUMENTS

| | | |
|---|---|---|
| EP | 1 700 572 A1 | 9/2006 |
| WO | 99/21502 A1 | 5/1999 |
| WO | 2009/032101 A2 | 3/2009 |

OTHER PUBLICATIONS

Zlowodzki et al., "The effect of shortening and varus collapse of the femoral neck on function after fixation of intracapsular fracture of the hip", Nov. 2008, JBJS [Br], vol. 90-B, No. 11, 1487-94, accessed Aug. 22, 2014.*

*Primary Examiner* — Matthew Lawson
*Assistant Examiner* — Amy Sipp
(74) *Attorney, Agent, or Firm* — Fitch Even Tabin & Flannery LLP

(57) ABSTRACT

A bone plate system for repair of a proximal humeral head fracture, which includes a fixation plate having a main body and a depending alignment flange, a plurality of elongated compression screws to extend through the intact humeral head into the cortical bone of the fractured portion and a cover plate. With the fixation plate in place, fastened to the humerus, the cover plate is in turn fastened to the fixation plate and provides a defined amount of clearance in a region adjacent the heads of the compression screws to allow measured backout of the screws upon settling of the fractured bone portion at the fracture site.

10 Claims, 4 Drawing Sheets

(56) References Cited

U.S. PATENT DOCUMENTS

| | | |
|---|---|---|
| 5,053,039 A | 10/1991 | Hofmann et al. |
| 5,462,547 A | 10/1995 | Weigum |
| 5,578,034 A | 11/1996 | Estes |
| 5,681,313 A | 10/1997 | Diez |
| 5,938,664 A | 8/1999 | Winquist et al. |
| 5,951,558 A | 9/1999 | Fiz |
| 6,096,040 A | 8/2000 | Esser |
| 6,235,034 B1 | 5/2001 | Bray |
| 6,406,478 B1 | 6/2002 | Kuo |
| 6,413,259 B1* | 7/2002 | Lyons et al. ............ 606/295 |
| 6,468,278 B1 | 10/2002 | Muckter |
| 6,595,993 B2* | 7/2003 | Donno et al. ............ 606/71 |
| 6,599,290 B2* | 7/2003 | Bailey et al. ............ 606/86 B |
| 6,623,486 B1 | 9/2003 | Weaver et al. |
| 6,652,525 B1 | 11/2003 | Assaker et al. |
| 6,695,846 B2 | 2/2004 | Richelsoph et al. |
| 7,004,944 B2 | 2/2006 | Gause |
| 7,060,067 B2 | 6/2006 | Needham et al. |
| 7,273,481 B2 | 9/2007 | Lombardo et al. |
| 7,604,657 B2 | 10/2009 | Orbay et al. |
| 7,731,718 B2 | 6/2010 | Schwammberger et al. |
| 7,758,616 B2 | 7/2010 | LeHuec et al. |
| 8,764,809 B2* | 7/2014 | Lorenz et al. ............ 606/286 |
| 2004/0210217 A1* | 10/2004 | Baynham et al. ............ 606/61 |
| 2005/0015089 A1 | 1/2005 | Young et al. |
| 2005/0049594 A1 | 3/2005 | Wack et al. |
| 2005/0085818 A1* | 4/2005 | Huebner ............ 606/69 |
| 2005/0240187 A1* | 10/2005 | Huebner et al. ............ 606/69 |
| 2006/0085071 A1* | 4/2006 | Lechmann et al. ........ 623/17.11 |
| 2006/0100626 A1 | 5/2006 | Rathbun et al. |
| 2006/0122605 A1 | 6/2006 | Suh et al. |
| 2006/0293670 A1* | 12/2006 | Smisson et al. ............ 606/69 |
| 2007/0173839 A1* | 7/2007 | Running et al. ............ 606/69 |
| 2007/0173840 A1* | 7/2007 | Huebner ............ 606/69 |
| 2008/0140130 A1* | 6/2008 | Chan et al. ............ 606/280 |
| 2008/0255559 A1* | 10/2008 | Leyden et al. ............ 606/62 |
| 2008/0269807 A1 | 10/2008 | Simon et al. |
| 2009/0171396 A1* | 7/2009 | Baynham et al. ............ 606/280 |
| 2009/0234359 A1* | 9/2009 | Onoue et al. ............ 606/71 |
| 2009/0254129 A1 | 10/2009 | Tipirneni et al. |
| 2009/0326591 A1 | 12/2009 | Spencer |
| 2010/0030277 A1* | 2/2010 | Haidukewych et al. ...... 606/286 |
| 2010/0217332 A1* | 8/2010 | Daniels et al. ............ 606/305 |
| 2011/0264150 A1* | 10/2011 | Hansson et al. ............ 606/290 |
| 2012/0095466 A1* | 4/2012 | Winslow et al. ............ 606/71 |
| 2012/0179208 A1* | 7/2012 | Geissler et al. ............ 606/282 |

\* cited by examiner

BONE PLATE SYSTEM FOR REPAIR OF PROXIMAL HUMERAL FRACTURE

This application claims priority from U.S. Provisional Patent Application Ser. No. 61/431,258, filed Jan. 10, 2011, the disclosure of which is incorporated herein by reference.

FIELD OF THE INVENTION

The present invention relates to orthopedic products for repair of fractured bones and more particularly to bone plate systems for repair of a major bone of the skeleton of a vertebrate, such as a proximal humeral head fracture.

BACKGROUND OF THE INVENTION

Fractures of the proximal humerus can occur in patients of any age; however, these fractures have been found to occur more frequently in older patients, particularly elderly females who may suffer from osteoporosis. Such fractures usually occur in predictable fracture patterns and are commonly caused by falls where an arm was outstretched in an attempt to break the fall. Due to the compressive and varus forces about the shoulder, there is a tendency for the humeral head fragment to collapse in varus and settle distally.

Treatment of such fractures has, in past decades, tended to use a screw and fixation plate system where the fractured portion of the humeral head is first realigned, if displaced, and the proximal end of the humerus is then stabilized by multiple screws that attach a fixation plate to the surface of the humerus opposite from the surface where the fracture has occurred. Use of such plates for this purpose is well known and is shown, for example, in U.S. Pat. No. 7,604,657 and Published Application No. 2009/0326591. Such fixation or bone plates usually include a variety of holes, some of which are dedicated to elongated compression screws for passage through the head of the humerus into the fractured segment, whereas other holes are dedicated for the passage of a K-wire for alignment purposes, or for sutures for use in compressing the fractured bone part against the humerus, or for screws to securely mount the plate to the cortical bone of the humerus.

A wide variety of mechanisms have been developed for locking these elongated compression screws to the fixation plate so as to prevent incidental subsequent movement of the screws that might result in screw back-out, which has been felt to be undesirable toward retaining the fractured section of the humeral head in alignment. Some of these locking systems have used a variety of inserts for positioning within the cavities in the fixation plate where the heads of the elongated screws would reside, such as those shown in U.S. Pat. Nos. 5,578,034; 6,695,846; 7,004,944 and 7,273,481, designed to lock the heads. Alternative solutions have resulted in employment of a variety of plates or detents which are fastened in some manner so as to abut the heads of the elongated screws and thus positively block any back-out of the screw heads within the fixation plate; examples of such are shown in U.S. Pat. Nos. 4,794,918; 6,406,478; 6,413,259; 6,652,525 and 7,060,067, and in Published Patent Application 2006/0122605.

Over the years, it has been found that, during post-surgery, the fractured portion of the humeral head may frequently settle upon the closing of the fracture gap, and the amount of such settling can often be significant. The result has often been the protrusion of the pointed tips of the elongated compression screws through the cortical bone of the fractured portion, resulting in the emergence of these pointed tips in the articular surface of the humerus.

Effective locking plate systems particularly suited for the treatment of proximal humeral head fractures which avoid potential screw tip protrusion into the articular surface of the humeral head have accordingly been sought.

BRIEF SUMMARY OF THE INVENTION

A bone plate system is provided which includes a fixation plate having a variety of holes, including holes for elongated threaded compression screws that will extend into the cortical bone of the fractured portion of a humeral head and holes for the passage of other screws to fasten the fixation plate to the cortical bone of the humerus which it abuts, and a cover plate. When the cover plate is installed onto the implanted fixation plate, its interior surface is spaced a precise distance from the heads of the elongated compression screws to provide a clearance region; this region provides space into which a defined extent of screw back-out is allowed.

The system design is such that parallel, slightly oversize holes are drilled through the intact humeral head, which holes have a diameter such that the elongated compression screws can freely pass therethrough so as to reach and enter the cortical bone of the fractured portion, into which they will become threadably connected. With the elongated compression screws threaded into the cortical bone of the fractured portion and with the fixation plate securely fastened to the humerus via a plurality of fastening screws, the fracture portion is pulled into contact with the intact humeral head. The cover plate is then installed; this plate is proportioned to fit over and envelop the region wherein of the heads of all of the elongated compression screws lie. The cover plate is recessed to provide a clearance of between about 2 and about 6 mm between the end faces of the heads of the compression screws and the interior surface of the cover plate. As a result, when settling of the fractured portion of the humeral head occurs as a result of its compression against the major portion of the humerus, some measured back-out of the compression screws is allowed; the heads may move longitudinally in the clearance region for 2-6 mm before making contact with the interior surface of the cover plate. During such movement, sliding engagement of the shanks of the compression screws within the walls of the holes of the fixation plate through which the compression screws pass continues to stabilize the secure connection of the fractured portion to the remainder of the intact humerus, as the fixation plate is itself securely affixed to the humerus by fastening screws.

In one particular aspect, the invention provides a bone plate system for repair of a fracture of a major bone of the skeleton of a vertebrate, which system comprises a fixation plate having a main body which includes (a) a plurality of holes for passage therethrough of screws for fastening said fixation plate to the surface of an intact bone within which a fracture has occurred to create a fractured separate bone portion thereof and (b) a plurality of holes through which elongated compression screws can be passed which will extend through drilled passageways in the bone and screw into cortical bone of said fractured separate portion thereof, a plurality of fastening screws, a plurality of said elongated compression screws having threaded distal end portions, a cover plate which, when installed as a part of the implanted bone plate system, has an inner surface that is spaced a defined distance from the heads of said elongated compression screws to provide a gap between said inner surface and the outer surface of said fixation plate, and fastening means for securing said cover plate to said fixation plate with said inner surface spaced between about 2 and about 6 mm from heads of said elongated screws so that, upon compression of said fractured portion and said bone, pointed tips of said threaded end portions of said elongated compression screws remain connected within cortical bone of said fractured bone portion while said heads of said elongated compression screws can move longitudinally into the gap between said fixation plate outer surface and said cover plate inner surface.

In another particular aspect, the invention provides a bone plate system for repair of a fracture of a major bone of the skeleton of a vertebrate, which system comprises a fixation plate having a main body including a head section and a stem section, which plate includes (a) a plurality of holes for passage therethrough of screws for fastening said fixation plate to the surface of an intact bone within which a fracture has occurred to create a fractured separate bone portion thereof and (b) a plurality of holes in said head section through which elongated compression screws can be passed which will extend through drilled passageways in the bone and screw into cortical bone of said fractured separate portion thereof, a plurality of fastening screws, a plurality of said elongated compression screws having threaded distal ends portions, and an integral stabilization flange which depends from said head section of said fixation plate and is aligned at an angle of about 70 degrees to 90 degrees thereto, which flange allows said fixation plate to be precisely aligned on the intact bone portion to facilitate precise placement of said elongated compression screws.

DETAILED DESCRIPTION OF THE PREFERRED EMBODIMENTS

Figure 1:
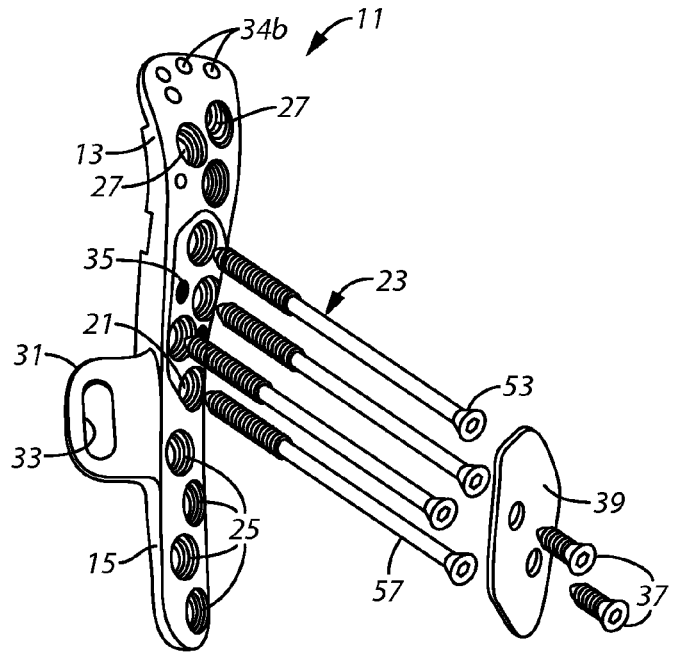
FIG. 1 is an exploded perspective view of a portion of a bone plate system embodying various features of this invention which includes a humeral head fixation plate, four elongated compression screws, a cover plate, and two locking screws for securing the cover plate to the fixation plate.
Figure 2:
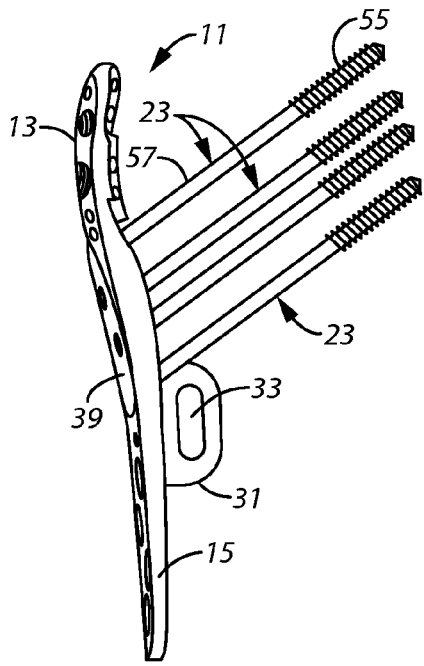
FIG. 2 is a side view of the bone plate system of FIG. 1 shown with the elongated compression screws and the cover plate in their operative positions.

FIG. 1 shows a bone or fixation plate 11 designed particularly for treating a fracture of the proximal humerus, which is made of rigid material such as a biocompatible metal or metal alloy, e.g. titanium, stainless steel, titanium-aluminum-niobium alloys, etc. The fixation plate 11 has a main body 12 which comprises a head section 13 and stem section 15. As best seen in FIG. 2, the fixation plate 11 is contoured so as to follow the general shape of the proximal end of the humerus, with the head section 13 lying juxtaposed with a surface of the humeral head and with the stem section 15 juxtaposed with a central elongated section of the humerus.

Figure 4:
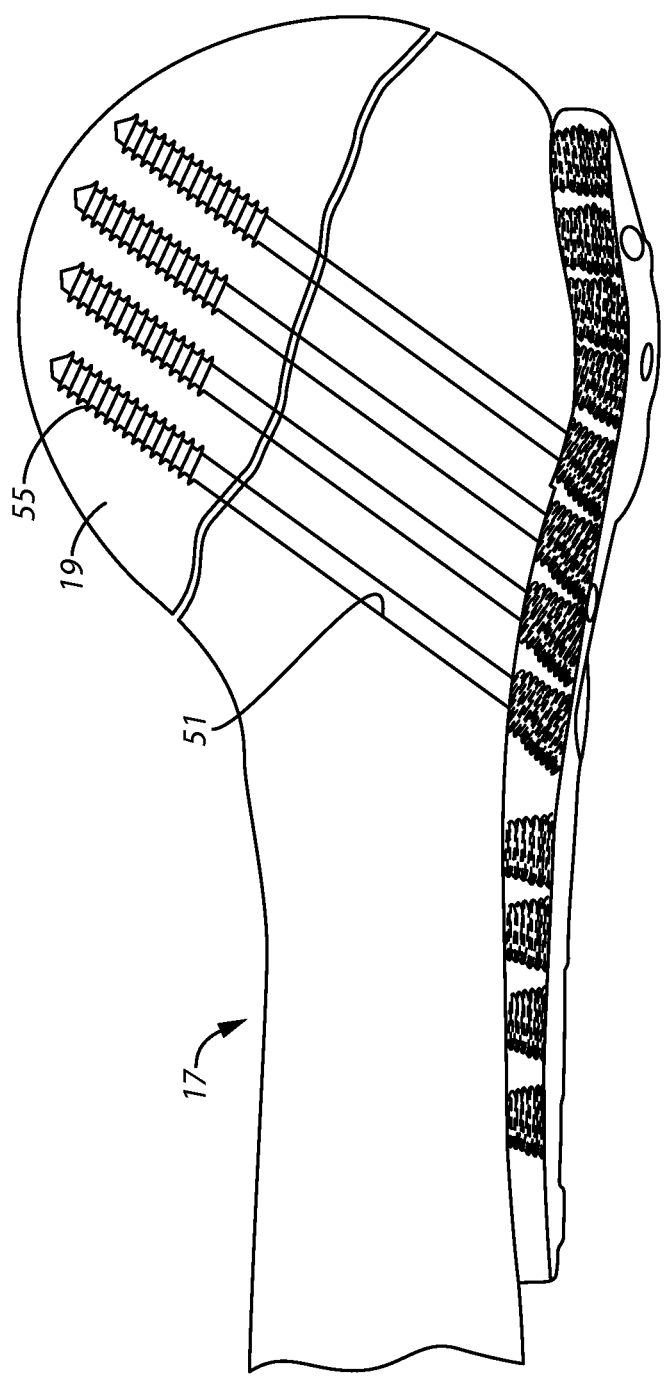
FIG. 4 is a cross sectional schematic view taken along a line through the center of each of the holes showing the bone plate system of FIG. 1 implanted in a fractured humeral head.

The fixation plate 11 is designed for treatment of a fracture of the humerus 17 where a portion 19 of the head of the humerus has been fractured and separated from the remainder of the bone. FIG. 4 depicts such a repair of a humeral head fracture showing the proximal end region of the humerus 17 and the fractured portion of the humeral head 19 as it might be repaired using a bone plate system embodying features of the present invention. The head section 13 of the fixation plate 11 includes a plurality of holes 21, in this case four, through which elongated compression screws 23 are passed; these four screws are designed to threadably connect to the cortical bone of the detached or fractured portion 19 of the humeral head as depicted in FIG. 4. To afford good purchase which assures that the fractured portion can be pulled into tight contact with the surface of the intact humeral head, it is important that the threaded ends are seated deeply into the cortical bone so their end tips are close to the outer surface.

The fixation plate 11 also contains a plurality of holes for fastening screws to affix the plate to the surface of the intact humerus. Four holes 25 are located in the stem 15 distally of the four holes 21 for the compression screws, and four more holes 27 are located in the head section 13 proximally of the four holes 21. In the illustrated embodiment, these holes 25 and 27 will accommodate 8 fastening screws 29 (see FIG. 6) that will be screwed into cortical bone of the humerus 17 to securely fasten the fixation plate 11 thereto. The holes 25 and 27 may be optionally threaded as depicted.

The fixation plate 11 also carries a stabilizing flange 31 which depends from the stem section 15 of the plate and is aligned at an angle of between about 70 degrees and 90 degrees to the main body 12 of the plate. This flange 31 has a longitudinally extending elongated hole or slot 33 and is designed to lie adjacent the side surface of the humerus 17 to which it can be secured, if desired, by a screw or other fastener inserted through the elongated hole 33. This flange 31 and the elongated hole 33 may cooperate to effect initial precise positioning of the plate 11 upon the surface of the intact humerus.

The fixation plate also includes various other holes, such as holes 34a, through which K-wires may be passed for use during the implantation of the bone plate system by the surgeon, and holes 34b through which other fasteners or sutures can be passed. In particular, the fixation plate 11 includes two small threaded holes 35, which are located and created to receive two lock screws 37 that are used to mount a cover plate 39 to the exterior surface of the fixation plate 11 once implantation of the plate is essentially completed.

The cover plate 39 is shaped and proportioned to fit atop and obscure the four holes 21 that receive the elongated compression screws 23 that are used to reunite the fractured humeral head portion 19 to the remainder of the intact humerus 17. The embodiment of the cover plate 39 shown includes two countersunk openings 41 which receive the cover plate lock screws 37 and are aligned with the two threaded holes 35 in the fixation plate. The exterior surface of the cover plate 39 is essentially smooth except for the two countersunk openings 41, and its interior surface is recessed (see FIG. 5) so that there is an outer rim 43 which extends around the periphery of the cover plate that surrounds an essentially flat, central interior surface region 45. The rim 43 and the flat surface 45 form a boundary of a recess 47 having a depth of between about 2 to 6 mm, and preferably between 3 and 5 mm, e.g. between about 3 to 4 mm.

Figure 5:
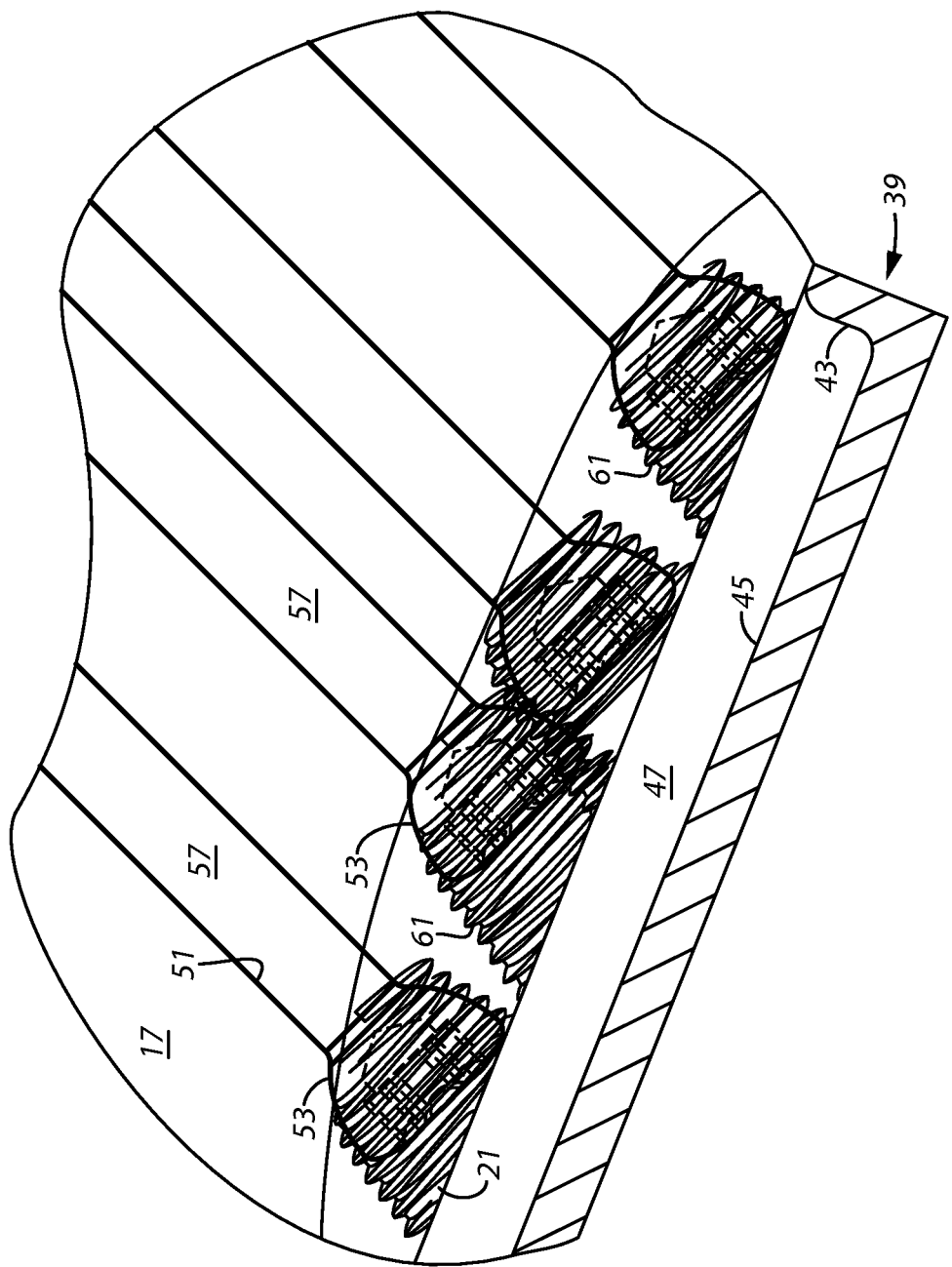
FIG. 5 is a fragmentary view, enlarged in size, of a portion of the bone plate system shown in FIG. 4, emphasizing the relationship between the heads of the elongated compression screws and the cover plate as such might exist immediately following orthopedic surgery to repair a fractured humeral head.

As best seen perhaps in FIG. 5, the four holes 21 through which the elongated compression screws are passed may be optionally threaded, if desired for a purpose to be explained hereinafter. In any respect, the holes 21 through the fixation plate are preferably aligned so as to have four parallel centerlines; thus, the four compression screws 23 will extend parallel to one another through four parallel passageways 51 drilled in the intact humerus 17, through the spongy cancellous bone, traversing the fracture site and enter the cortical bone at the surface of the fractured portion 19 of the humeral head. The compression screws 23, as seen in FIGS. 1 and 5, have socket heads 53 which may, for example, be of smooth, generally hemispherical or ovoid exterior shape. The distal ends 55 of the compression screws 23 are threaded; however, the shanks 57 of the screws are preferably smooth and of a diameter similar to that of the threaded portion or slightly greater than the threaded portion. Prior to installation, four parallel passageways 51 are drilled through intact humeral head using an appropriate jig or guide; these four parallel passageways are slightly oversized so there will be no direct frictional connection of the shanks 57 of the compression screws to the bone of the intact portion of the humerus 17. The walls of the outer portions of the four holes 21, which may be thought of as countersinks 61, may optionally be threaded, and are sized such that the shank 57 of each screw is relatively tightly constrained by the wall surface of an inner or neck portion of the hole where the hole opens onto the interior surface of the fixation plate; however, the generally hemispherical surface of the head 53 is juxtaposed within the threaded countersink region 61 which is proportioned so that the head can rotate freely. All four heads 53 of the compression screws 23 originally reside entirely within the confines of the countersunk four holes 21, as seen in FIG. 5, and the pointed end tips 59 are seated in the cortical bone of the fractured portion 19 as shown in FIG. 4. Although compression screws 23 having socket heads are preferred, Philips head screws or screws having heads of other design might alternatively be employed.

Figure 3:
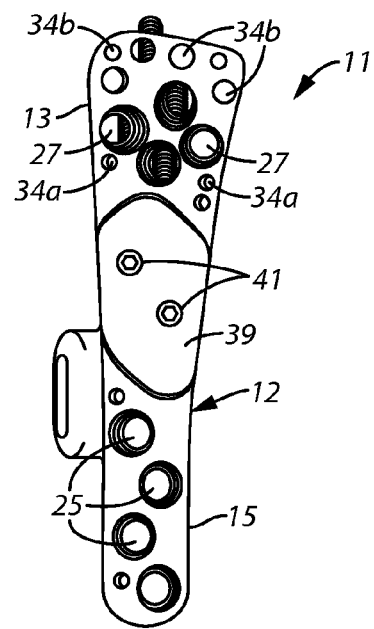
FIG. 3 is a front view of the bone plate system shown in FIG. 2.

Once the four compression screws 23 are in place with the threaded ends 55 extending into the cortical bone of the fractured portion 19 of the humeral head, and with the fracture site in alignment as shown in FIG. 4, the four screws 23 are tightened so as to pull and compress the fractured portion 19 against the intact humerus 17; then the cover plate 39 is fastened to the fixation plate 11 so as to cover socket heads 53 and obscure the four openings 21. Fastening of the cover plate 39 to the fixation plate 11 can be done by any appropriate securing mechanism. In the illustrated embodiment, such fastening is simply effected by threading two lock screws 37 through countersunk openings 41 in the cover plate 39 into the two aligned, threaded holes 35 in the fixation plate 11 to tightly affix the cover plate in the orientation shown in FIGS. 3, 4 and 5.

As best seen in enlarged cross sectional view FIG. 5, the recess 47 provided within the cover plate 39 spaces the interior surface 45 of the cover plate a precise desired distance from the nearest point of approach of the flat front surface of each of the four socket-head compression screws 23. It has been shown that a minimum distance of at least about 2 mm should be provided for the gap between the flat interior surface 45 and the screw heads 53, and more preferably the depth of the gap is not greater than about 5 or 6 mm.

As previously indicated, it is important that the elongated compression screws 23 extend sufficiently deeply into the cortical bone of the fractured portion 19 of the humeral head to provide adequate purchase to assure compression and ultimate fixation at the fracture site that will result in the repair of the fractured humeral head. However, such an orientation creates the potential of extrusion/protrusion of the pointed tips 59 of the compression screws 23, out of the fractured portion 19 and into the articular surface of the humerus, when the heads of the screws 23 are rigidly clamped or otherwise affixed within the openings of the fixation plate 11, as has been the general practice. In contrast, when using the embodiment shown in FIGS. 1 to 5, should settling occur as a result of further compression at the fracture site, because there is no direct, rigid connection of the compression screws 23 to the bone of the intact humerus, or to the plate 11, the fixation plate 11 would not prevent longitudinal movement of the screws 23. Instead, the design of the cover plate/fixation plate combination is such as to permit measured longitudinal movement of the heads 53 of the compression screws 23 in the region of the holes 21 and the recess 47 within the cover plate 39 for at least a minimum distance of about 2 mm and more preferably for a distance of about 3 to about 5 mm. This arrangement positively guards against extrusion of the compression screw pointed ends 59 into the articular surface of the humeral head; at the same time, it retains adequate stability of the overall repair through confinement of the four heads 53 within the holes 21 and through the sliding contact between the shank 57 of each of the four screws and the circular wall of each hole where it leads to the inner surface of the fixation plate 11.

As an example of such a repair of a proximal humerus fracture, a fixation plate 11 of the appropriate size would be chosen and fitted to the humerus 17, and one or more K-wires might be installed. A guide might then be substituted for the plate to be implanted, and four parallel passageways 51 drilled in the humerus 17 that are just slightly oversized relative to the shanks 57 of the compression screws 23 to be used. Thereafter, with the fractured portion 19 of the humerus 17 likely sutured to the head of the intact humerus, the fixation plate 11 is positioned on the intact humerus assisted by the K-wires, and the stabilizing flange 31 is juxtaposed with the lateral surface of the humerus so that a screw (not shown) can optimally be inserted through the center of the elongated hole 33. Final positioning of the plate 11 is then facilitated by movement guided by the elongated hole 33 in the flange 31, and the four compression screws 23 are passed through the four holes 21. Using self-tapping threads, the threaded portions 55 of the screws 23 are threaded into the fractured humeral portion 19. These four socket-head screws 23 are then tightened to align and compress the fractured portion 19 with the remainder of the intact humeral head across the fracture site from the position shown in FIG. 4, and so as to extend deeply into the cortical bone, terminating near the outer articular surface.

Once this reconnection of the fractured portion 19 to the humeral head is completed, the fixation plate 11 would be fastened to the humerus 17 by drilling holes and installing eight fastening screws 29 through the holes 25 and 27. Any K-wires would then be removed if not already removed. If not earlier inserted, a further fastener might then be inserted through the elongated hole 33 in the lateral flange 31. With the fixation plate 11 thus securely fastened to the intact humerus, a final tightening of the four compression screws 23 might be made. Then the cover plate 39 would be installed using the two locking screws 37 to fasten it in place where it overlays and obscures the heads 53 of the four elongated compressions screws.

Thereafter, should settling occur between the fractured portion 19 and the intact humerus 17, movement of the screws will be along the path of least resistance; in other words, the shanks 57 of the compression screws 23 can slide longitudinally within the humerus with the socket-containing heads 53 moving longitudinally in the holes 21 into the minimum gap or recess 47 of at least about 2 mm. It has been found that the provision of such a gap is sufficient to preclude protrusion of the pointed tips 59 of the compression screws 23 out of the fracture portion in the articular region, which occurrence would likely result in the need for a further operation to correct.

Figure 8:
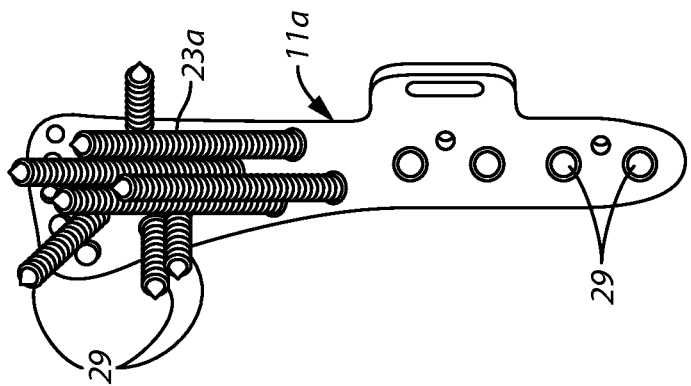
FIG. 8 is a rear view of the bone plate system shown in FIG. 6.
Figure 6:
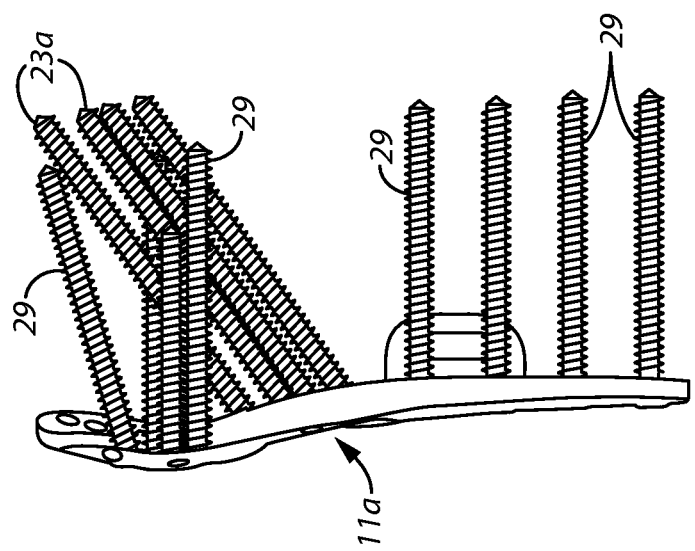
FIG. 6 is a side view of an alternative use of a humeral head fixation plate of the general type shown in FIG. 1 in combination with four elongated compression screws of different design and 8 fastening screws assembled therewith, illustrating the orientation in which they might reside when used to treat a fracture of the proximal humerus.
Figure 7:
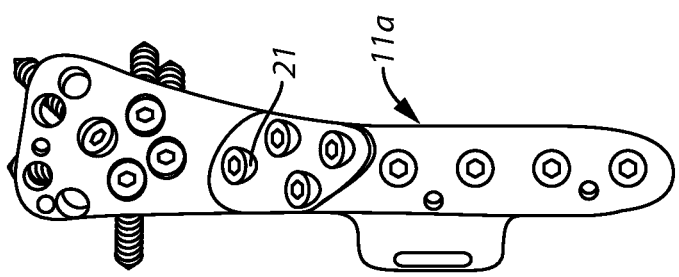
FIG. 7 is a front view of the bone plate system shown in FIG. 6 with the screws 23a removed.

As previously mentioned, the holes 21 of the fixation plate may be optionally threaded. Shown in FIGS. 6, 7 and 8 is a generally similar fixation plate 11*a* wherein use is made of such threaded holes 21. Should, for whatever reason, a surgeon feel that use of the bone plate system of FIGS. 1-5 might not be desired for repair of a particular fracture, the fixation plate 11*a* might be used with four elongated compression screws 23*a* that are threaded for their entire length. Such screws 23*a* might be affixed to the plate 11*a* by any suitable locking mechanism known in the art in combination with the threads in the holes 21. FIG. 6 shows such an arrangement where four such compression screws 23*a*, that are parallel to one another, are shown extending through the four holes 21 aligned so they would connect to a fracture portion of a humeral head. FIG. 7 shows the plate with the 4 compression screws removed so the screw threads can be seen. Eight fastening screws 29 are also shown extending through the holes 25 and 27 where they would extend into the cortical bone of the intact humerus and affix the plate 11*a* thereto. In this bone plate system, known locking arrangements in combination with the threads of the four holes 21 might be used that would prohibit back-out of the four compression screws 23*a*. Alternatively, a modified cover plate might be used having plugs that would appropriately abut the front surfaces of socket head screws and prevent any back-out. Thus, by providing the optional threads in the four holes 21, such a fixation plate is adapted for use both in the improved bone plate system with the recessed cover plate 39, as well as in a traditional arrangement where the compression screws 23*a* are locked against any back-out should a surgeon, for whatever reason, wish to employ such an arrangement.

Although the invention has been described with regard to the best mode presently known to the inventors, it should be understood that various changes and modification as would be obvious to one having ordinary skill in the art may be made without departing from the scope of the invention, which is set forth in the claims appended hereto. For example, although the bone plate system has been described and illustrated with regard a proximal humeral head fracture repair, it should be understood that it embodies principles that might be advantageously incorporated in repair of fractures of other load-bearing bones in vertebrates.

Particular features of the invention are emphasized in the claims which follow.

The invention claimed is:

1. A bone plate system for repair of a fracture of a major bone of a skeleton of a vertebrate, which system comprises:
    a fixation plate having a main body which includes (a) an outer surface having a recessed portion formed therein, (b) a plurality of holes for passage therethrough of fastening screws for fastening said fixation plate to a surface of an intact bone within which a fracture has occurred to create a fractured separate bone portion thereof and (c) a plurality of holes formed in the recessed portion through which elongated compression screws can be passed which will extend through drilled passageways in the intact bone and screw into cortical bone of said fractured separate portion thereof,
    a plurality of said fastening screws,
    a plurality of said elongated compression screws having heads and threaded distal end portions,
    a cover plate which, when installed as a part of the implanted bone plate system, has an inner surface that is spaced a defined distance from the heads of said elongated compression screws to provide a gap between said inner surface and the recessed portion of said fixation plate, said cover plate having a peripheral protruding lip that contacts the recessed portion of said fixation plate and surrounds a central region of said inner surface, and
    fasteners for securing said cover plate to said fixation plate with said inner surface spaced said defined distance of between about 2 and about 6 mm from the heads of said elongated screws so that, upon compression of said fractured portion and said intact bone, pointed tips of said threaded end portions of said elongated compression screws remain connected within the cortical bone of said fractured bone portion while said heads of said elongated compression screws can move longitudinally into the gap between said fixation plate recessed portion and said cover plate inner surface.

2. The bone plate system according to claim 1 wherein said cover plate inner surface has an essentially flat central region.

3. The bone plate system according to claim 1 wherein said defined distance is between about 3 and 5 mm.

4. The bone plate system according to claim 1 wherein said holes through which the compression screws pass are aligned with parallel centerlines.

5. The bone plate system according to claim 1 wherein said holes through which the compression screws pass have countersinks which form outer portions thereof.

6. The bone plate system according to claim 5 wherein said holes through which the compression screws pass have inner wall portions that slidably receive and stabilize smooth shank sections of the compression screws.

7. The bone plate system according to claim 5 wherein said countersinks are threaded.

8. The bone plate system according to claim 1 wherein said fasteners comprise two locking screws that are received in threaded holes in said fixation plate.

9. The bone plate system according to claim 1 wherein a stabilization flange depends from said main body aligned at an angle of about 70 degrees to 90 degrees thereto.

10. The bone plate system according to claim 9 wherein said stabilization flange includes a longitudinally extending elongated hole.

* * * * *